(12) United States Patent
Kishida et al.

(10) Patent No.: US 8,002,411 B2
(45) Date of Patent: Aug. 23, 2011

(54) FUNDUS CAMERA

(75) Inventors: Nobuyoshi Kishida, Musashino (JP);
Tomoyuki Iwanaga, Yokohama (JP);
Hideyuki Ohban, Kawaguchi (JP);
Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/432,626

(22) Filed: Apr. 29, 2009

(65) Prior Publication Data
US 2009/0279051 A1    Nov. 12, 2009

(30) Foreign Application Priority Data
May 9, 2008    (JP) .................................. 2008-122916

(51) Int. Cl.
*A61B 3/14*    (2006.01)
*A61B 3/10*    (2006.01)
(52) U.S. Cl. ....................................... 351/206; 351/205
(58) Field of Classification Search ........... 351/200–246
See application file for complete search history.

(56) References Cited

U.S. PATENT DOCUMENTS

| | | | | |
|---|---|---|---|---|
| 4,412,728 A | * | 11/1983 | Sakane et al. | 351/206 |
| 4,469,416 A | * | 9/1984 | Isono | 351/206 |
| 5,196,872 A | * | 3/1993 | Beesmer et al. | 351/206 |
| 5,572,266 A | * | 11/1996 | Ohtsuka | 396/18 |

FOREIGN PATENT DOCUMENTS

| | | |
|---|---|---|
| JP | 5-95907 A | 4/1993 |
| JP | 8-275921 A | 10/1996 |

* cited by examiner

*Primary Examiner* — Mohammed Hasan
(74) *Attorney, Agent, or Firm* — Canon U.S.A., Inc., IP Division

(57) ABSTRACT

A fundus camera includes a fundus photographing optical system including an image-recording image sensor for photographing a fundus image via a focusing lens, a focus target having a plurality of regions for forming light fluxes passing through a plurality of different areas on pupil of a subject's eye, and a focus drive unit for driving the focusing lens based on positions of a plurality of images of the focus target in an image captured by the image-recording image sensor and on contrast of the images.

23 Claims, 16 Drawing Sheets

FIG. 4A
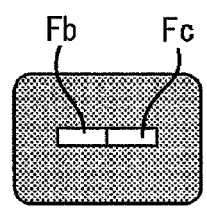 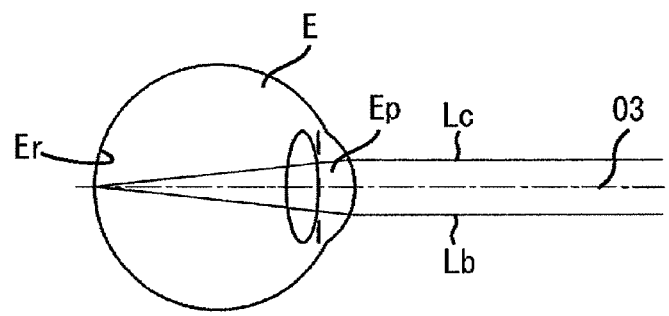
FIG. 4B
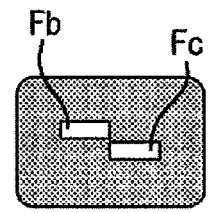 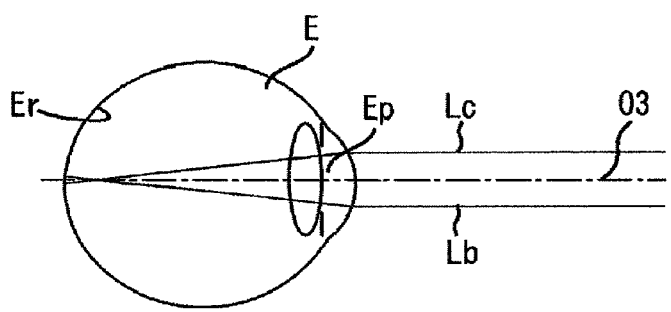
FIG. 4C
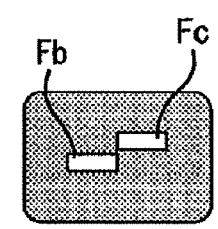 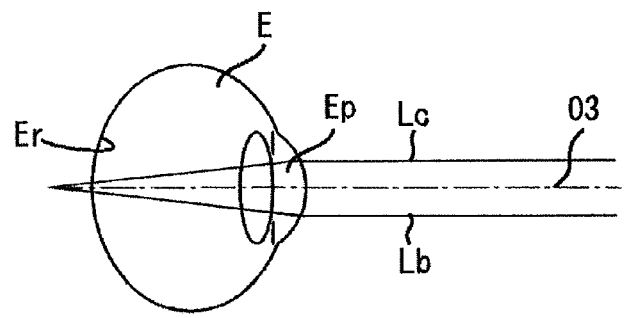

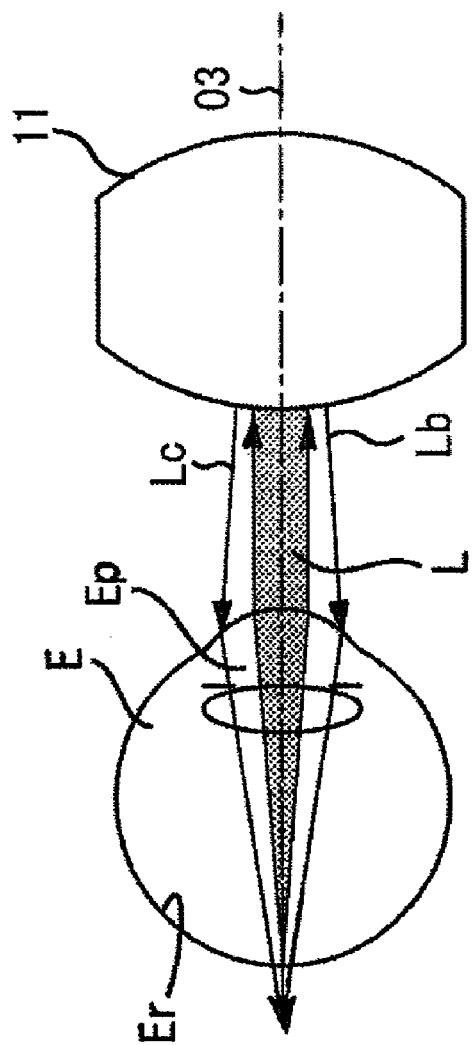
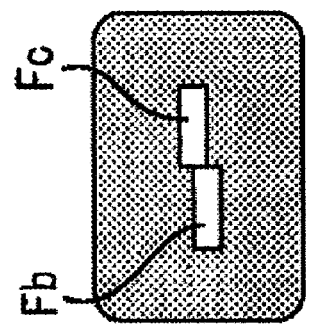
FIG. 7

FUNDUS CAMERA

BACKGROUND OF THE INVENTION

1. Field of the Invention

The present invention relates to a fundus camera used for photographing a fundus of a subject's eye in an ophthalmologist's office or the like.

2. Description of the Related Art

Hitherto, a fundus camera has been known, which includes a projecting unit for projecting a focus split target light flux being split on the pupil of a subject's eye onto the fundus thereof and an observing/photographing unit, provided with a focusing lens, for observing and photographing the fundus thereof. Both of the units are interlockingly moved in the direction of an optical axis. An operator can easily adjust the focus of the fundus camera by observing focus split target images formed on the fundus of the subject's eye and bringing the focus split target images into a predetermined positional relationship, i.e., aligning the focus split target images in a line. In addition, a device has been known, which achieves autofocus by capturing focus split target images and detecting the positions of the focus split target images.

Techniques for facilitating focusing a fundus camera on the fundus of a subject's eye have been known, which project a focus split target being split on the pupil of a subject's eye onto the fundus and observe images of the projected focus split target via a focusing lens of a fundus observing/photographing optical system, and which perform focusing by observing a positional relationship of the focus split target images.

In addition, techniques for achieving autofocus have been known, which perform imaging of focus split target images projected onto a subject's eye fundus and which perform focusing by observing a positional relationship of the focus split target images.

Japanese Patent Application Laid-Open No. 5-95907 discusses a fundus camera that performs imaging of two focus split images projected onto a subject's eye fundus and detects a focus state based on positions of the two focus split target images while attenuating the brightness of the target.

Japanese Patent Application Laid-Open No. 8-275921 discusses an ophthalmologic apparatus that projects a focus target onto the fundus of a subject's eye and performs imaging of focus target images using a photographing optical system, thereby detecting a focus state.

However, in order to eliminate reflection light from a subject's eye cornea, conventional fundus cameras are constructed such that a fundus illumination light flux or a focus split target light flux and an observing/photographing light flux are respectively incident upon different areas in the vicinity of a subject's eye pupil. Accordingly, in a case where an aberration of an optical system of a subject's eye varies among individuals, when a subject's eye fundus is photographed only by setting the positions of the focus split target images in a predetermined positional relationship, a focusing error may be caused in some subject's eye. Consequently, a fundus image may be out of focus.

SUMMARY OF THE INVENTION

The present invention is directed to a fundus camera capable of photographing a subject's eye fundus without causing a focus deviation even in a case where a subject's eye has an aberration.

According to an aspect of the present invention, a fundus camera includes an illumination optical system including an illumination unit configured to illuminate a fundus of a subject's eye, a fundus photographing optical system including an image-recording image sensor configured to capture a fundus image via an objective lens and a focusing lens, a focus target located in the illumination optical system at a position conjugate with the fundus of the subject's eye and configured to have a plurality of regions for forming light fluxes respectively passing through different areas of a pupil of the subject's eye to form a plurality of focus target images on the fundus, an observing images sensor located in the photographing optical system at a position conjugate with the fundus of the subject's eye and configured to capture the plurality of focus target images reflected from the fundus, a focus drive unit configured to drive the focus target and/or the focusing lens, a target image position detection unit configured to detect positions of the plurality of focus target images on the observing image sensor, a first focus detection unit configured to calculate a first driving amount of the focus drive unit based on the positions of the plurality of focus target images detected by the target image position detection unit, a drive control unit configured to drive and control the focus drive unit based on the first driving amount calculated by the first focus detection unit, and a second focus detection unit configured to detect a change in the focus target images based on an output of the observing images sensor during a driving operation of the focus drive unit and to calculate a second driving amount of the focus drive unit based on the detected change.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIGS. 4A through 4C illustrate functions of a focus target.

FIG. 7 illustrates a subject's eye having a spherical aberration and focus target light fluxes and an observing/photographing light flux in the vicinity of an objective lens.

DETAILED DESCRIPTION OF THE EMBODIMENTS

Various exemplary embodiments, features, and aspects of the invention will be described in detail below with reference to the drawings.

Figure 1:
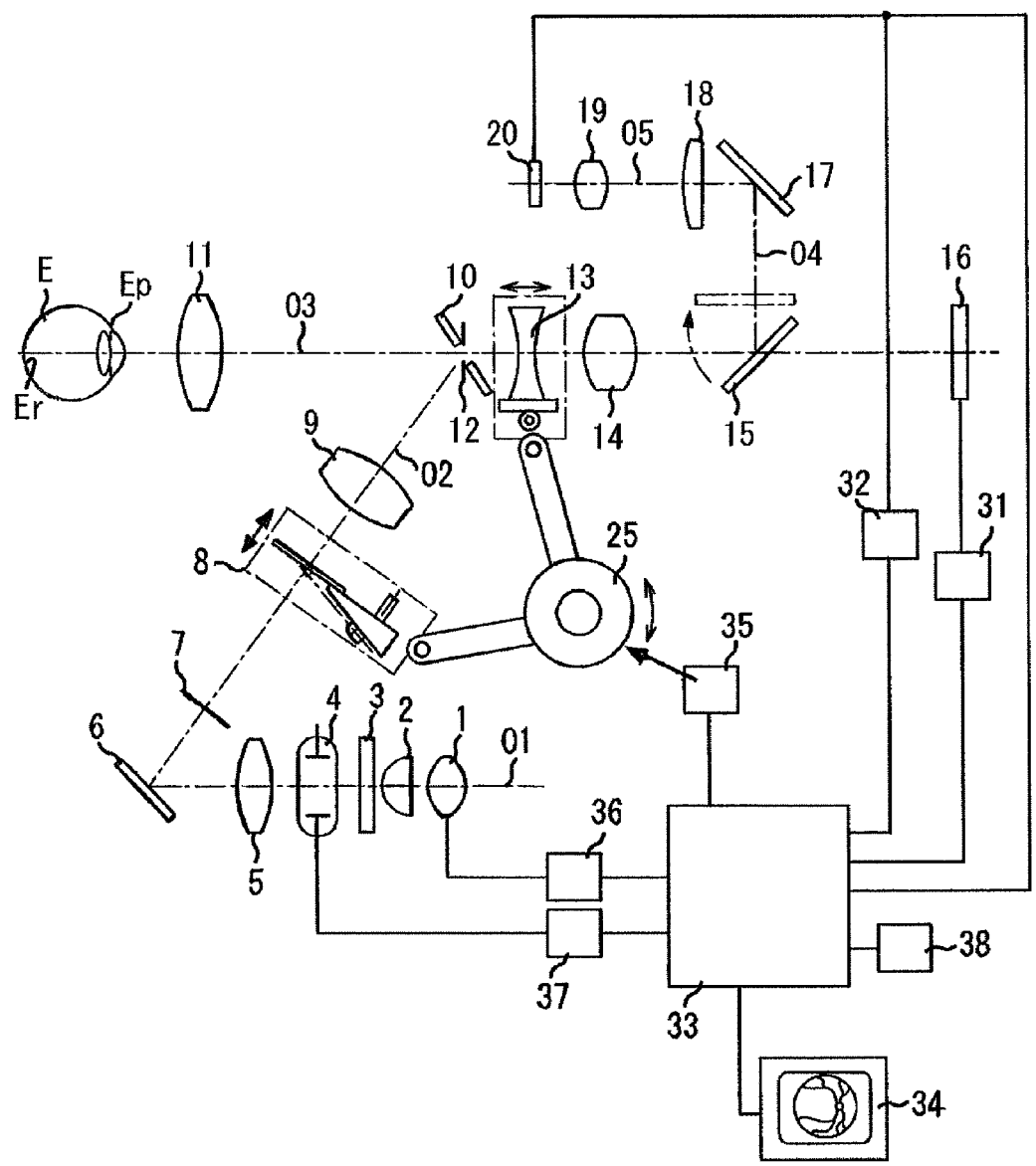
FIG. 1 illustrates a configuration of a fundus camera according to an exemplary embodiment of the present invention.

FIG. 1 illustrates a configuration of a fundus camera according to a first exemplary embodiment of the present invention. An illumination optical system is constructed on optical axes O1 and O2. An observing light source 1, such as a halogen lamp, configured to emit stationary light, a condenser lens 2, a filter 3 configured to transmit infrared light and to interrupt visible light, a photographing light source 4, such as a flash unit, a lens 5, and a mirror 6 are arranged on the optical axis O1. A ring diaphragm 7 having an annular opening, a focus target projection unit 8, a relay lens 9, and a perforated mirror 10 having a central opening are sequentially arranged on the optical axis 2 extending in a reflection direction from the mirror 6.

An objective lens 11 facing a subject's eye E is located on an optical axis O3 extending in a reflection direction from the perforated mirror 10. In addition, a photographing diaphragm 12 is provided in a hole portion of the perforated mirror 10. A focusing lens 13, a photographic lens 14, a flip-up mirror 15, and an image-recording image sensor 16 are sequentially arranged behind the perforated mirror 10. Thus, a fundus photographing optical system is constructed.

A mirror 17 configured to reflect infrared light and to transmit visible light is located on an optical axis O4 extending in a reflection direction from the flip-up mirror 15. A field lens 18, a lens 19, and an observing image sensor 20 are sequentially arranged on an optical axis O5 extending in a reflection direction from the mirror 17. Each of the image-recording image sensor 16 and the observing image sensor 20 is located at a position that is optically conjugate with that of a fundus $E_r$ of the subject's eye E.

Figure 2A:
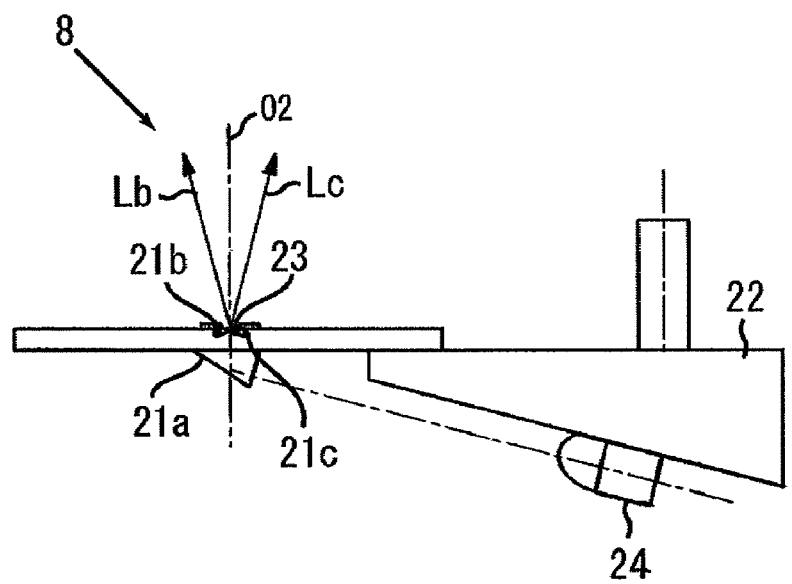
FIGS. 2A and 2B are a side view and a front view of a focus target projection unit, respectively.
Figure 2B:
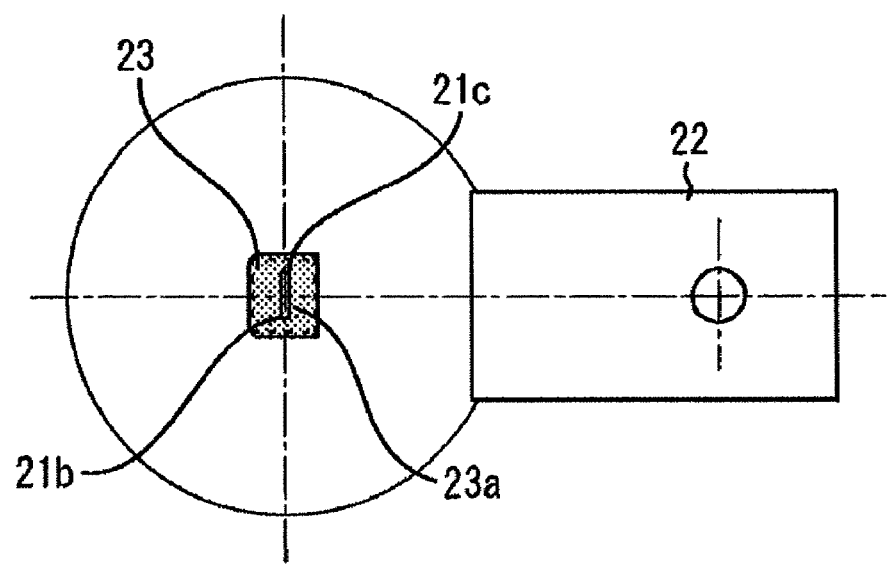

FIGS. 2A and 2B are a side view and a plan view of the focus target projection unit 8, respectively. As illustrated in FIGS. 2A and 2B, the focus target projection unit 8 includes a focus split prism 22 having prism portions 21a, 21b, and 21c, a focus target 23 having a rectangular opening portion 23a, and a focus target illuminating light emitting diode (LED) 24.

The focus target projection unit 8 on the optical axis O2 and the focusing lens 13 on the optical axis O3 are connected to each other by a focus link mechanism 25 and are interlockingly movable in the directions of the optical axes O2 and O3, respectively. That is, the focus link mechanism 25 drives the focus target projection unit 8 and the focusing lens 13 such that the focus target 23 of the focus target projection unit 8 and the image-recording image sensor 16 are located so as to be optically conjugate with each other.

An output of the image-recording image sensor 16 is connected to the control unit 33 via an image processing unit 31. An output of the observing image sensor 20 is connected to the control unit 33 via a focus detection unit 32. In addition, a monitor 34 and a focus drive unit 35 for driving the focus link mechanism 25 are connected to the control unit 33. The control unit 3 outputs to the monitor 34 an observation image captured by the observing image sensor 20 and a still image captured by the image-recording image sensor 16.

A photographing switch 38 is connected to the control unit 33. In addition, an output of the control unit 33 is connected to the observing light source 1 via an observing light source control unit 36 for controlling adjustment of the amount of light, turn-on, and turn-off of the observing light source 1. An output of the control unit 33 is also connected to the photographing light source 4 via a photographing light source control unit 37 for controlling adjustment of the amount of light, turn-on, and turn-off of the photographing light source 4.

Devices other than the monitor 34 and the photographing switch 38 are mounted on an optical base (not shown). Thus, an optical unit of the fundus camera is constructed. The optical unit is mounted on a stage unit.

When the fundus camera is used, the control unit 33 controls the observing light source control unit 36 to turn on the observing light source 1. A light flux emitted from the observing light source 1 is condensed by the condenser lens 2. The filter 3 cuts out visible light of incident light from the photographing light source 4. However, only infrared light thereof is transmitted by the filter 3. Further, the transmitted light is further transmitted by the photographing light source 4, such as a flash unit. Then, a ring light flux is formed by the lens 5, the mirror 6, and the ring diaphragm 7. Subsequently, the light flux is deflected by the relay lens 9 and the perforated mirror 10 in the direction of the optical axis O3. The deflected light flux illuminates the fundus $E_r$ of the subject's eye E via the objective lens 11.

The light flux reaching the fundus $E_r$ is reflected and scattered. Then, light to be formed into a fundus reflection image is reflected from the subject's eye E. The reflected light passes through the objective lens 11, the photographing diaphragm 12, the focusing lens 13, and the photographic lens 14. Then, the light is deflected by the flip-up mirror 15 and the mirror 17. The deflected light is formed into a fundus reflection image on the observing image sensor 20 via the field lens 18 and the lens 19. Then, the control unit 33 causes the monitor 34 to display the fundus image captured by the observing image sensor 20.

The operator performs fine adjustment of alignment of the optical unit with the subject's eye E while observing the fundus image displayed on the monitor 34. Subsequently, the operator performs focus adjustment, which will be described below. Then, the operator presses the photographing switch 38 and performs photographing of a fundus image.

As illustrated in FIG. 2A, a light flux emitted from the focus target illumination LED 24 is deflected in the direction of the optical axis O2 by the prism portion 21a of the focus split prism 22. Then, the deflected light flux reaches each of the prism portions 21b and 21c. The prism portions 21b and 21c respectively have prism-faces the inclination angles of which are symmetrical with respect to the optical axis O2. The light flux reaching each of the prism portions 21b and 21c passes through the rectangular opening portion 23a of the focus target 23 illustrated in FIG. 2B. Thus, two focus target light fluxes Lb and Lc illustrated in FIG. 2A are formed so as to be symmetric with respect to the optical axis O2. Then, the focus target light fluxes Lb and Lc reach the subject's eye E via the relay lens 9, the perforated mirror 10, and the objective lens 11.

Figure 3:
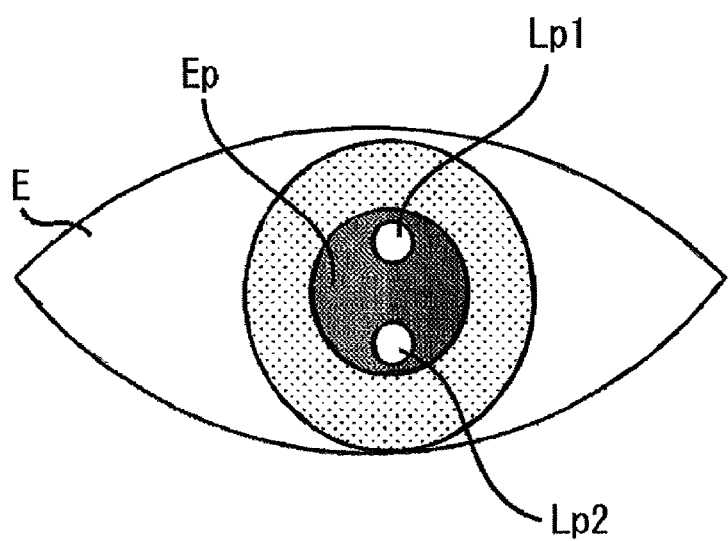
FIG. 3 illustrates a position on a pupil of a subject's eye, through which each focus target light flux passes.

FIG. 3 illustrates a position Lp1 on a pupil $E_p$ of the subject's eye E, through which the focus target light flux Lb passes, and a position Lp2 on the pupil $E_p$ of the subject's eye E, through which the focus target light flux Lc passes.

FIGS. 4A through 4C illustrate manners in each of which the focus target fluxes Lb and Lc reach the fundus $E_r$ of the subject's eye E, and functions of focus target images Fb and Fc on the fundus $E_r$, which are formed from the focus target light fluxes Lb and Lc, respectively. FIG. 4A illustrates a case where the fundus $E_r$ of the subject's eye E is optically conjugate with the focus target 23. Because the fundus $E_r$ is optically conjugate with the focus target 23, the two separated focus target light fluxes Lb and Lc are formed through a plurality of areas, which are different parts of the pupil $E_p$, into the target images Fb and Fc of the rectangular opening portion 23a of the focus target 23 on the fundus $E_r$, so that the target images Fb and Fc are located in a line.

FIG. 4B illustrates a case where the subject's eye E is more near-sighted, as compared with the subject's eye E illustrated in FIG. 4A. Because the fundus $E_r$ in the case illustrated in FIG. 4B is not optically conjugate with the focus target 23, the two separated focus target light fluxes Lb and Lc are formed into the target images Fb and Fc on the fundus $E_r$ so that, as viewed in FIG. 4B, the target image Fb is shifted upward from the position thereof illustrated in FIG. 4A, while the target image Fc is shifted downward from the position thereof illustrated in FIG. 4A.

FIG. 4C illustrates a case where the subject's eye E is more far-sighted, as compared with the subject's eye E illustrated in FIG. 4A. Because the fundus $E_r$ in the case illustrated in FIG. 4B is not optically conjugate with the focus target 23, the two separated focus target light fluxes Lb and Lc are formed into the target images Fb and Fc on the fundus $E_r$ so that, as viewed in FIG. 4C, the target image Fb is shifted downward from the position thereof illustrated in FIG. 4A, while the target image Fc is shifted upward from the position thereof illustrated in FIG. 4A.

According to an autofocus method employed in a conventional fundus camera, the focus target images Fb and Fc are detected and are then arranged in a line, so that the fundus $E_r$ and the focus target 23 are optically conjugate with each other. In a case where the focus target 23 of the focus target projection unit 8 and the image-recording image sensor 16 are set by the focus link mechanism 25 so as to be optically conjugate with each other, the fundus $E_r$ and the image-recording image sensor 16 are optically conjugate with each other. Consequently, the fundus $E_r$ is brought into focus.

However, in a case where an optical aberration is large due to a spherical aberration, astigmatism, or the like of the subject's eye E, even when the focus target images Fb and Fc are located in a line, the focus target images may not brought into focus.

Figure 5:
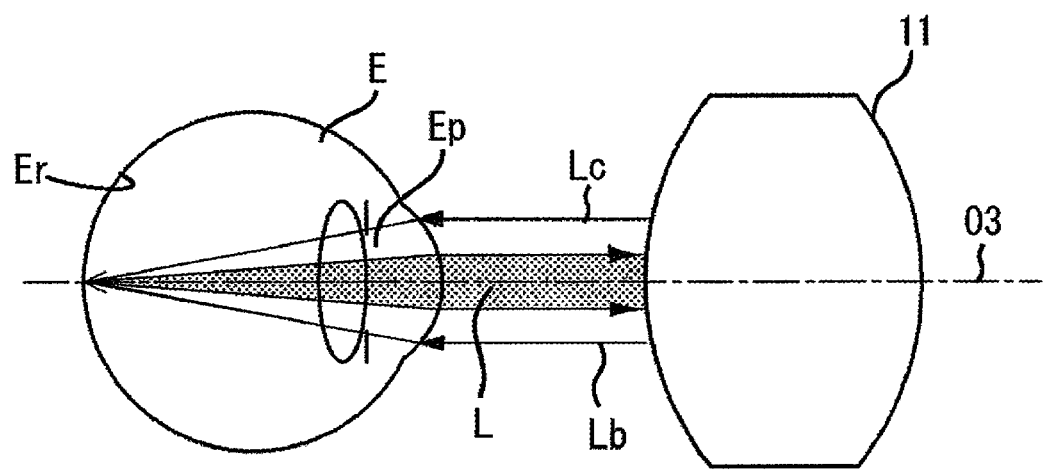
FIG. 5 illustrates a subject's eye and focus target light fluxes and an observing/photographing light flux in the vicinity of an objective lens.

FIG. 5 illustrates the subject's eye E and the focus target light fluxes Lb and Lc and the observing/photographing light flux L in the vicinity of the objective lens 11 in the present embodiment. The focus target light fluxes Lb and Lc pass through positions on the pupil $E_p$ of the subject's eye E, which are located away from the optical axis O3. The observing/photographing light flux L passes through a position on the pupil $E_p$, which corresponds to the center of the optical axis O3. In a case where the optical aberration of the subject's eye E is small, the depth of focus of the fundus camera is large. The fundus $E_r$ can be put into focus by aligning the focus target images Fb and Fc displayed on the monitor 38 in a line.

Figure 6:
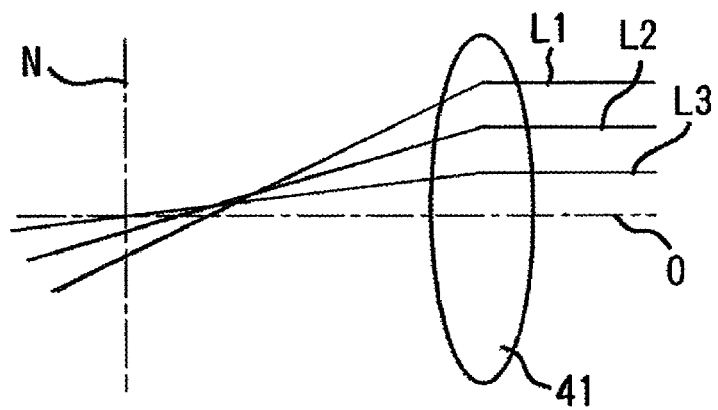
FIG. 6 illustrates a spherical aberration.

FIG. 6 illustrates a spherical aberration. It is assumed that, as viewed in FIG. 6, light rays L1, L2, and L3, which are parallel to the optical axis O and differ from one another in height from the optical axis O, are incident upon the lens 41 from the right side, as viewed in FIG. 6, towards a focal plane N of the lens 41. In a case where the lens 41 has a spherical aberration, the light ray L3, whose height from the optical axis O is lowest, passes through a position on the focal plane N, which is substantially closest to the optical axis O. However, the light rays L1 and L2 pass through positions on the focal plane N, which are located away from the optical axis O.

As described above, in a case where the aberration of the subject's eye E is large, the focus target light fluxes Lb and Lc and the observing light flux L pass through different areas on the pupil $E_p$. Accordingly, even when the focus target images Fb and Fc are arranged in a line, the images Fb and Fc are affected by the aberration of the lens 41. Thus, the fundus $E_r$ is not always brought into best focus.

FIG. 7 illustrates the subject's eye E having a large spherical aberration and the focus target light fluxes Lb and Lc and the observing/photographing light flux L in the vicinity of the objective lens 11. Because the subject's eye E has a large spherical aberration, best focus cannot be achieved by arranging the focus target images Fb and Fc in a line. The fundus $E_r$ is brought into focus by locating the focus target image Fb slightly downward from the position illustrated in FIG. 4A and the focus target image Fc slightly upward from the position illustrated in FIG. 4A.

Thus, aberrations, such as a spherical aberration and astigmatism, of human eyes vary among different individuals. Consequently, in a case where a subject's eye E has a large aberration, focus correction suitable for the aberration of the subject's eye E is needed.

Figure 8:
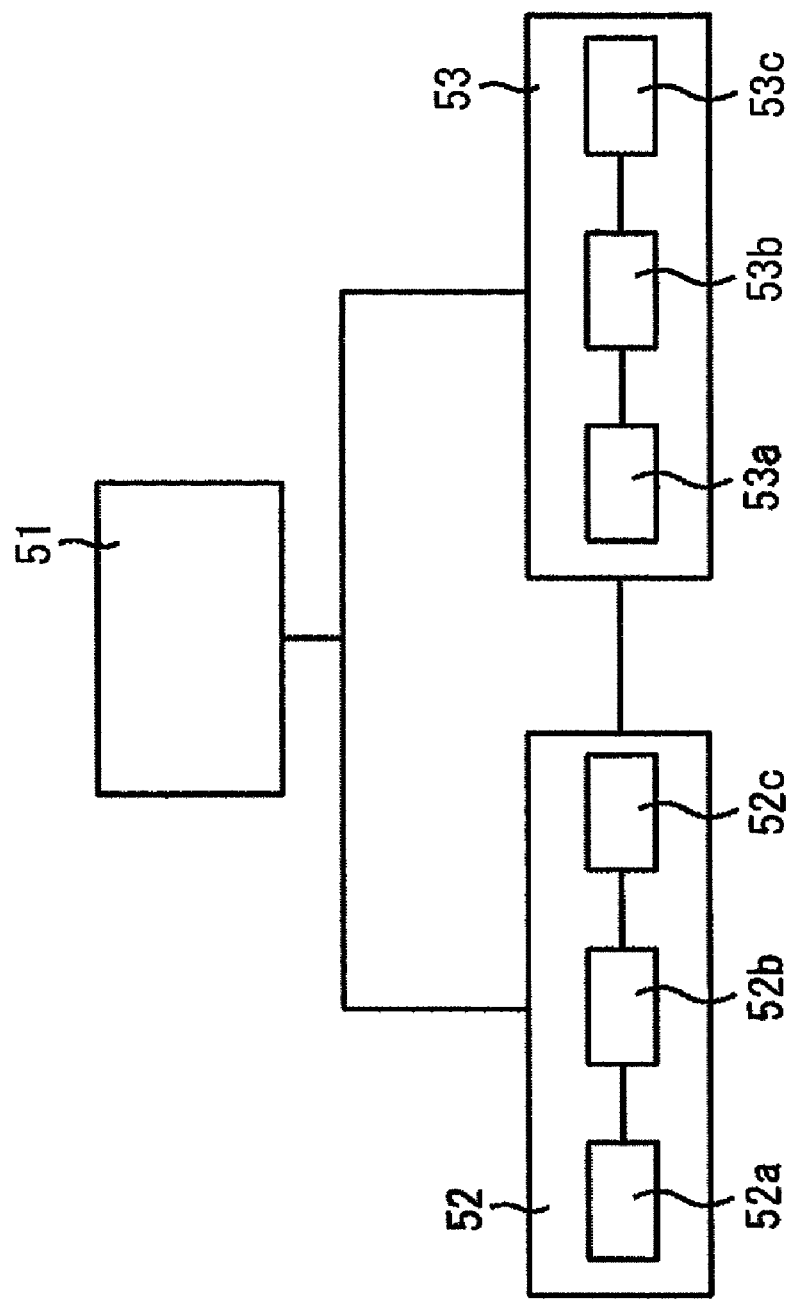
FIG. 8 illustrates a configuration of a focus detection unit.

FIG. 8 illustrates a configuration of the focus detection unit 32. An image memory 51, a first focus detection subunit 52, and a second focus detection subunit 53, which are used for focusing, are provided in the focus detection unit 32. An output of the observing image sensor 20 is connected to the image memory 51. An output of the image memory 51 is connected to both the first focus detection subunit 52 and the second focus detection subunit 53. The first focus detection subunit 52 and the second focus detection subunit 53 are connected to each other in order to synchronize start of focus detection at the first focus detection subunit 52 with that of focus detection at the second focus detection subunit 53. According to the present embodiment, the first focus detection subunit 52 and the second focus detection subunit 53 have a focus detection function based on detection of the positions of the focus target images Fb and Fc and another focus detection function based on detection of contrast thereof, respectively.

The first focus detection subunit 52 includes a focus target image detection subunit 52a, a focus target distance detection subunit 52b, and a focus driving amount calculation subunit 52c. The focus target image detection subunit 52a performs detection of positions of the focus target images Fb and Fc. The focus target distance detection subunit 52a performs detection of a distance between the two focus target images Fb and Fc. The focus driving amount calculation subunit 52c calculates a first driving amount according to the distance between the focus target images Fb and Fc.

The second focus detection subunit 53 includes a contrast detection subunit 53a, a contrast determination subunit 53b, and a focus driving amount calculation subunit 53c. The contrast detection subunit 53a detects contrast of a combination of the focus target images Fb and Fc. The contrast determination subunit 53b performs determination of the contrast. The focus driving amount calculation subunit 53c calculates a second driving amount based on a result of the determination of the contrast.

Figure 9:
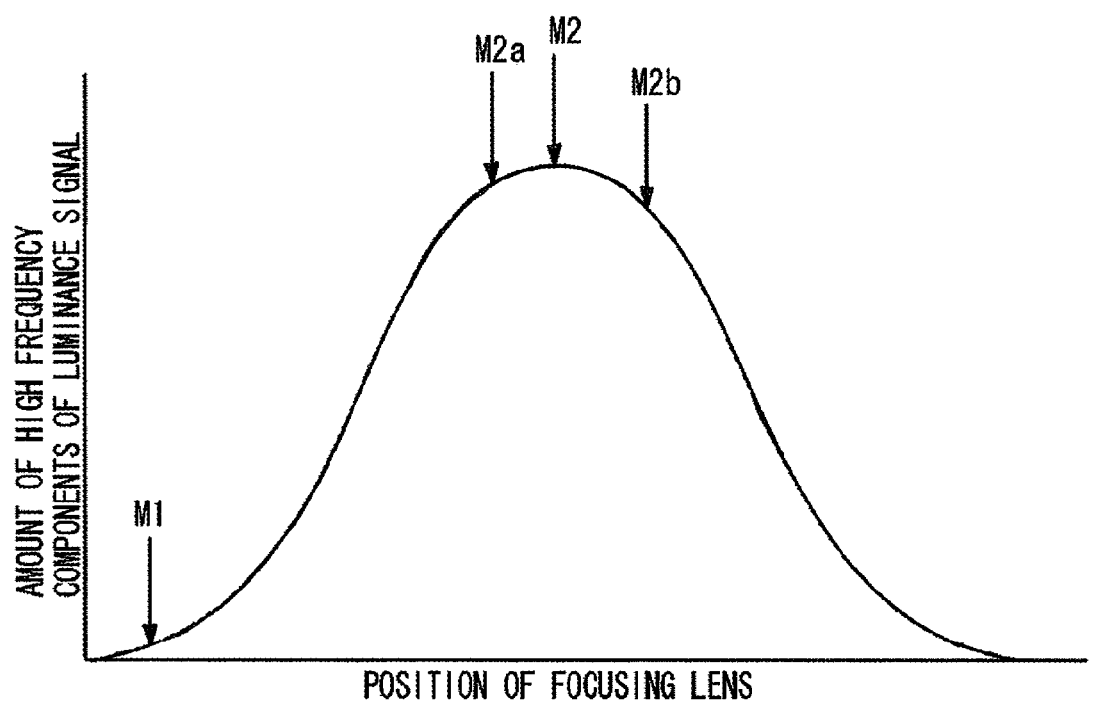
FIG. 9 illustrates a contrast detection principle.

FIG. 9 illustrates a contrast detection principle to be performed by the second focus detection subunit 53 to detect contrast of a combination of the focus target images Fb and Fc. This focus detection method utilizes the fact that the amount of high-frequency components of a luminance signal is maximized upon detecting in-focus of the focusing lens 13. The contrast detection subunit 53a extracts the high-frequency components of a luminance signal input by a band-pass filter or the like.

FIG. 9 illustrates the relationship between the position of the focusing lens 13 and the amount of high-frequency components of a luminance signal. The axis of abscissas represents the position of the lens 13. The axis of ordinates represents the amount of high-frequency components of a luminance signal. The amount of high-frequency components is maximized at an in-focus position M2 of the focusing lens 13. The amount of high-frequency components is small at a position M1 of the focusing lens 13 at which the focusing lens 13 is greatly out of focus.

Various methods for detecting, e.g., an edge of the target, a slope of the edge, and a target contrast obtained based on the highest luminance value and the lowest luminance value of a target image, or a half-width of the target can be considered as the focus detection method. However, in the following description of the present embodiment, a contrast detection method for extracting high-frequency components of a luminance signal is described by way of example. Alternatively, a method for detecting a target contrast based on the highest luminance value and the lowest luminance value of a target image is described in the description of a second exemplary embodiment to be described below.

Figure 10:
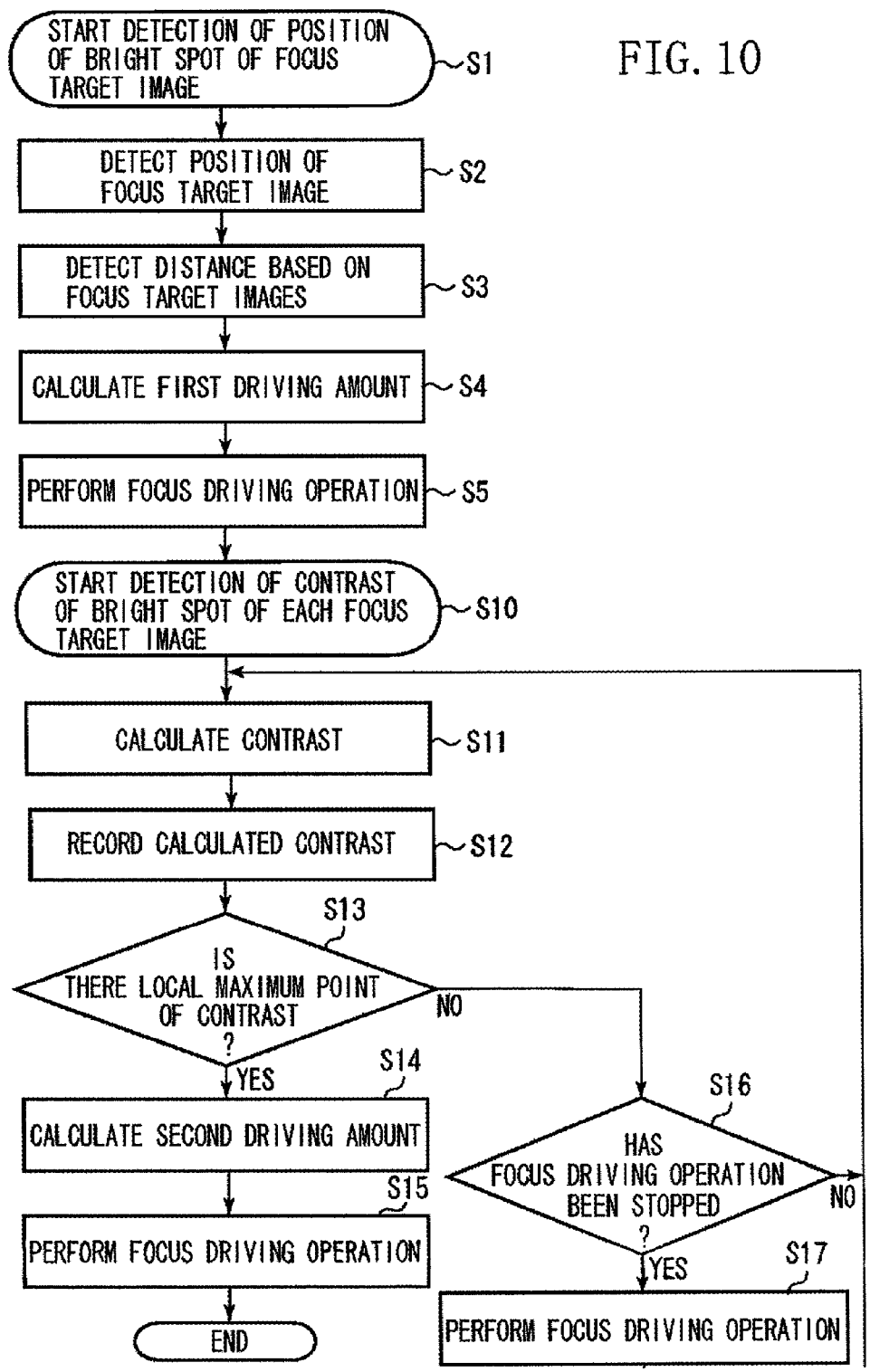
FIG. 10 is a flowchart illustrating a control method according to an exemplary embodiment of the present invention.

FIG. 10 is a flowchart illustrating an operation to be performed according to a control method of an exemplary embodiment of the present invention. When the focus target light fluxes Lb and Lc are projected onto the fundus Er, in step S1, detection of the positions of bright spots of the focus target images Fb and Fc is started. In step S2, the detection of the positions of the target images Fb and Fc is performed by the focus target image detection subunit 52a of the first focus detection subunit 52.

Figure 11:
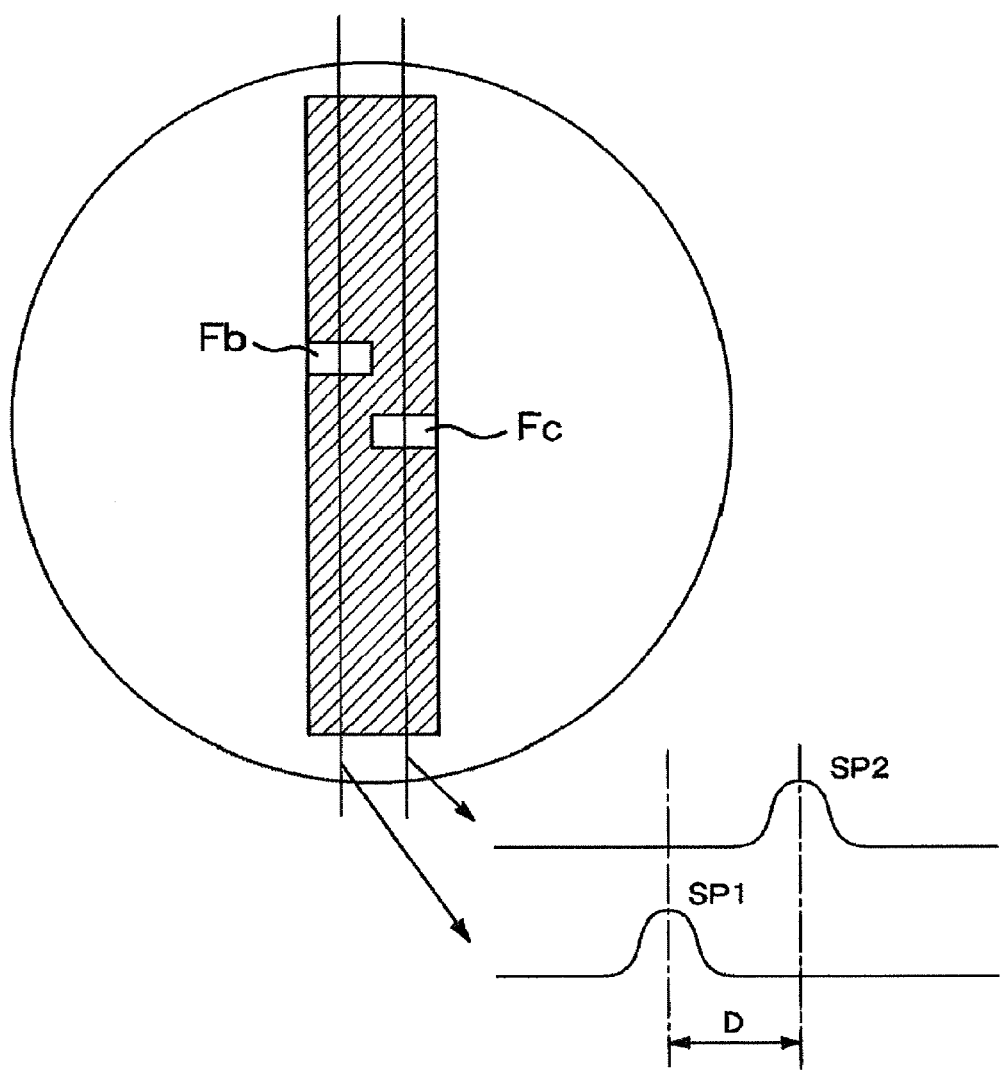
FIG. 11 illustrates an observation screen image before focusing.

The positional relationship between the focus target images Fb and Fc obtained in step S2 and the observation image is in a state of observation illustrated in FIG. 11. A position corresponding to a signal SP1 representing the focus target image Fb and a position corresponding to a signal SP2 representing the focus target image Fc are detected from image information recorded in the image memory 51. The image memory 51 does not need to record entire image information obtained by the observing image sensor 20. It is sufficient that the image memory 51 records image information representing images within a region in which the focus target images Fb and Fc can be detected.

In step S3, a distance D between the positions respectively corresponding to the signals SP1 and SP2 is detected by calculation by the focus target distance detection subunit 52b of the first focus detection subunit 52. In step S4, a first driving amount corresponding to the distance is calculated by the focus driving amount calculation subunit 52c. Step S5 is the last step of an autofocus process based on the detection of the positions of the focus target images Fb and Fc. In step S5, a focus driving (control) operation is performed using the focus drive unit 35 via the control unit 33 based on the first driving amount calculated in step S4.

Figure 12:
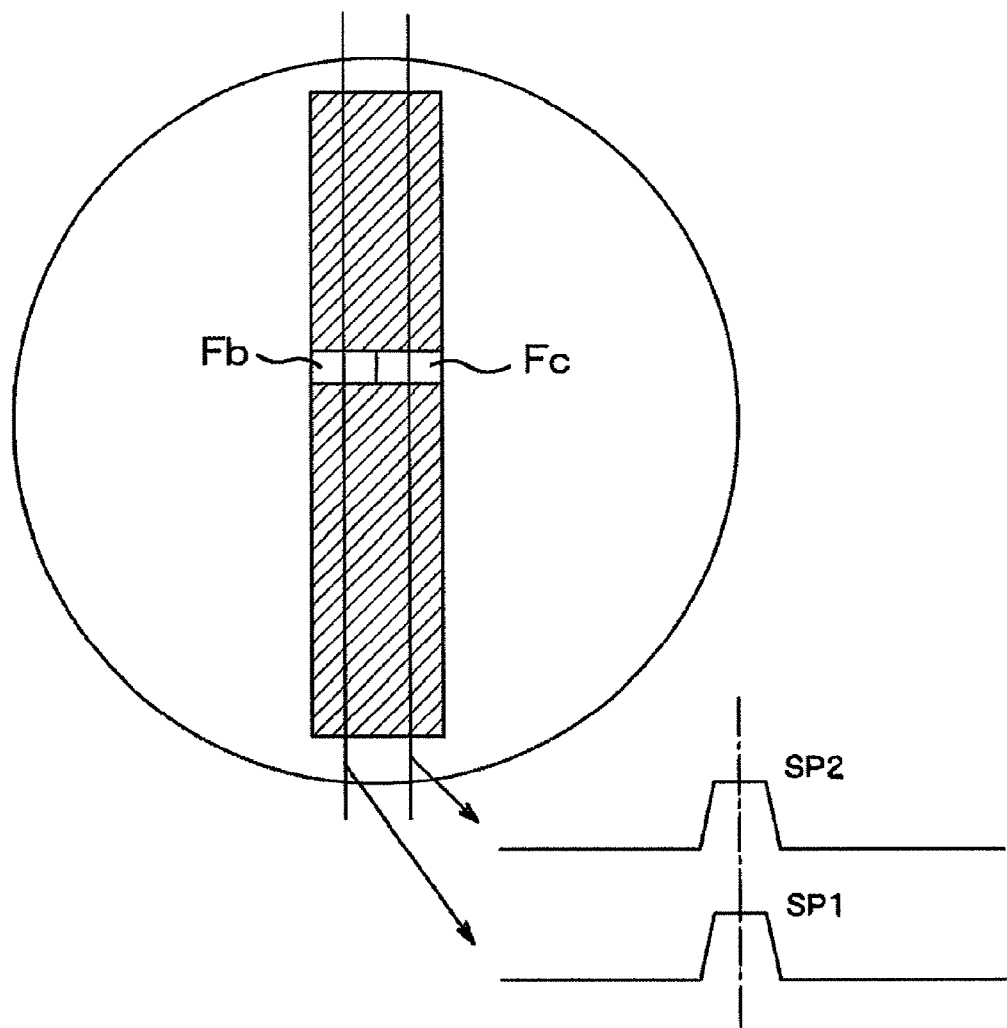
FIG. 12 illustrates a state of observation performed by a first focus detection unit after focusing.

Upon completion of focus driving in step S5, the relationship between the position corresponding to the signal SP1 representing the focus target image Fb and that corresponding to the signal SP2 representing the focus target image Fc is put into a state illustrated in FIG. 12. The above process up to this step is an autofocus method, which can also be performed by a conventional fundus camera. This autofocus method is called an "active phase difference detection method". More specifically, in a rough focus adjustment mode in which the focus target images Fb and Fc are arranged in a line, a target value of the driving operation can be calculated. Thus, a high-speed autofocus operation can be performed.

According to the present embodiment, in step S5, when a focus driving operation is started, i.e., while a focus driving operation is performed, a contrast detection operation for detecting the contrast of the combination of the focus target images Fb and Fc to be performed in step S10 is started. Thus, in a time period in which the state of observation is those illustrated in FIGS. 11 and 12, which are described in the description of steps S1 through S5, the detection of the contrast of the combination of the focus target images Fb and Fc is performed.

First, in step S11, the contrast of the combination of the focus target images Fb and Fc is calculated by the contrast detection subunit 53a. In step S12, the calculated value is recorded by the contrast determination subunit 53b. In step S13, the contrast determination subunit 53b detects whether the contrast value recorded in step S12 includes a position M2 illustrated in FIG. 9 as a local maximum point. At that time, it cannot be determined at the determination first made in step S13 whether each contrast value is a local maximum point. Thus, the process proceeds to step S16.

For convenience of description, a case in which a local maximum point is detected in step S13 is described below. In step S14, the driving amounts of the focus target images Fb and Fc are calculated by the focus driving amount calculation subunit 53c. Each of driving amounts of the focus target images Fb and Fc, which are calculated in step S14, is defined as a second driving amount from the detected position of the local maximum point.

Next, in step S15, a focus driving operation is performed based on focus driving amounts, i.e., the second driving amount calculated in step S14. Thus, the focusing lens 13 is moved to a position corresponding to the local maximum value of the amount of high-frequency components of the luminance signal, i.e., a position at which the contrast has a local maximum value. After the focusing lens 13 is driven, photographing of the fundus is performed.

According to the present embodiment, the calculation of the amount of driving of the focusing lens 13 in step S14 is performed according to a driving amount calculated in step S4 until the driving of the focusing lens 13 in step S5 is finished. Alternatively, another method can been considered, which interrupts the driving of the focusing lens 13 at the time of detecting a local maximum point in step S13 and which drives the focusing lens 13 to a position at which the contrast has a local maximum value.

In a case where no local maximum point is detected, the process proceeds to step S16. Then, if the driving of the focusing lens 13 is not finished in step S16, processing to be performed from step S11 to step S13 is repeated. If the driving of the focusing lens 13 is finished in step S16, the process proceeds to step S17. Then, after the driving of the focusing lens 13 by a predetermined amount, the processing to be performed from step S11 to step S13 is repeated. In step S16, the determination on whether the driving of the focusing lens 13 is finished is made based on the focus driving state (i.e., focusing-lens driving state) of the control unit 33.

The "driving the focusing lens 13 by a predetermined amount" is an amount at which the local maximum point, e.g., the position M2 illustrated in FIG. 9, can be detected. Alternatively, another method can be performed, which interrupts, after the process proceeds to step S17, the driving of the focusing lens 13 at the time of detecting a local maximum point in step S13 in the middle of the predetermined amount of the driving of the focusing lens 13.

Regardless of whether processing to be performed in step S17 is performed, processing to be performed in steps S11 and S12 is continued while the driving of the focusing lens 13 is continued, until a local maximum point is detected in step S13. In step S10, the driving of the focusing lens 13 is performed as the control operation to be performed in step S5 according to the present embodiment.

Hereinafter, the relationship between the contrast and the state of observation in a case in which processing in step S17 is performed, and the relationship therebetween in a case in which such processing is not performed are described. In the state of observation illustrated in FIG. 10, the contrast is determined by the high-frequency components at a position M1 illustrated in FIG. 9. First, if the processing in step S17 is not performed, a position M2 at which the amount of high-frequency components is maximized is detected before the driving of the focusing lens 13 performed in step S5 according to the driving amount calculated in step S4 illustrated in FIG. 10 is finished. Before the state of observation illustrated in FIG. 11 is changed to the state of observation illustrated in FIG. 12, the position M2 at which the amount of high-frequency components is maximized is detected. That is, in the state of observation illustrated in FIG. 12, a position M2b illustrated in FIG. 9 is detected.

Figure 13:
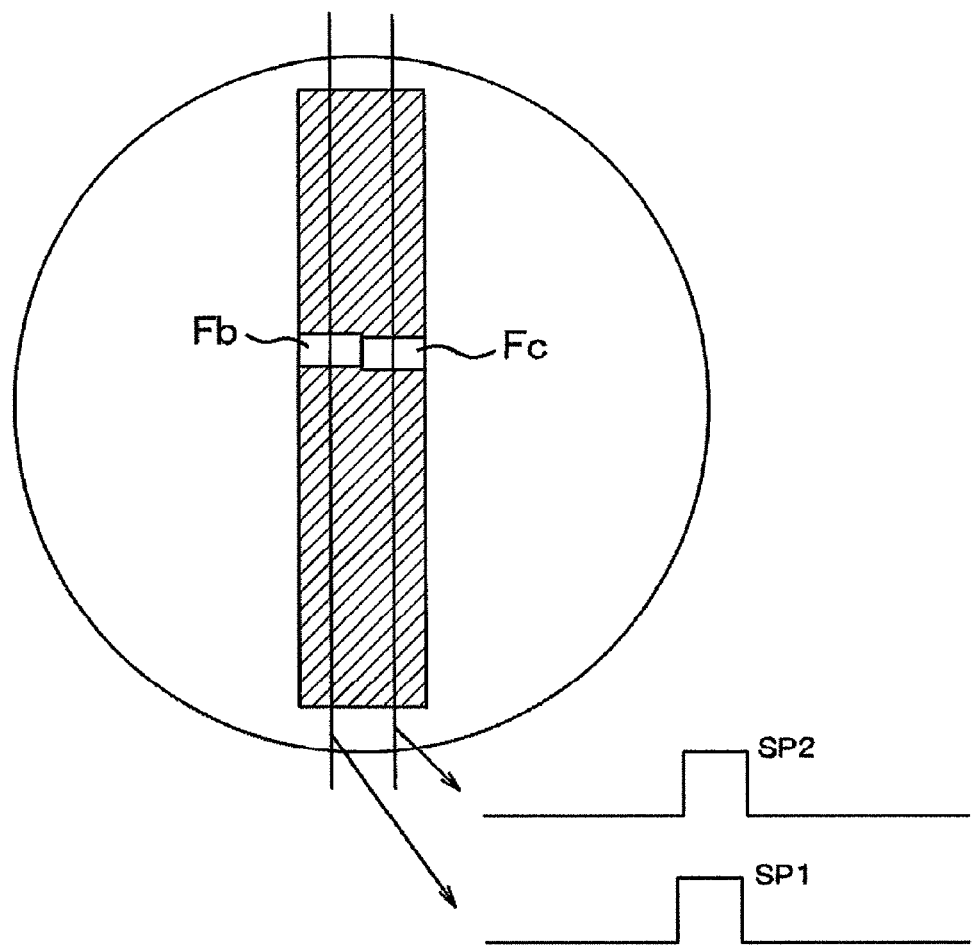
FIG. 13 illustrates a state of observation performed by a second focus detection unit before focusing.

In this case, a second driving amount from the position, at which the local maximum point is detected, is calculated in step S14 illustrated in FIG. 10. Thus, the focusing lens 13 is driven by an amount corresponding to a distance of movement from the position M2 illustrated in FIG. 9 to the position M2b. Consequently, the state of observation is changed from that of observation illustrated in FIG. 12 to that of observation illustrated in FIG. 13. As is apparent from the foregoing description, a direction of the driving of the focusing lens 13 from the position M2 illustrated in FIG. 9 to the position M2b is opposite to a direction of driving the focusing lens 13, which is performed in step S5.

Next, in a case where the processing in step S17 is not performed, the position M2 at which the amount of high-frequency components is maximized is not detected based on the first driving amount calculated in step S4 illustrated in FIG. 10, even when the driving of the focusing lens 13 is performed in step S5. Accordingly, even when the state of observation illustrated in FIG. 11 is changed to that of observation illustrated in FIG. 12, the position M2 at which the amount of high-frequency components is maximized is not detected. That is, in the state of observation illustrated in FIG. 12, the focusing lens 13 is placed at the position M2a illustrated in FIG. 9. Thus, in step S17, the driving of the focusing lens 13 by a predetermined amount is performed. Then, in step S13, the position M2 at which the amount of high-frequency components is maximized is detected. Subsequently, such processing is performed until the focusing lens 13 is moved slightly towards the position M2b.

Figure 14:
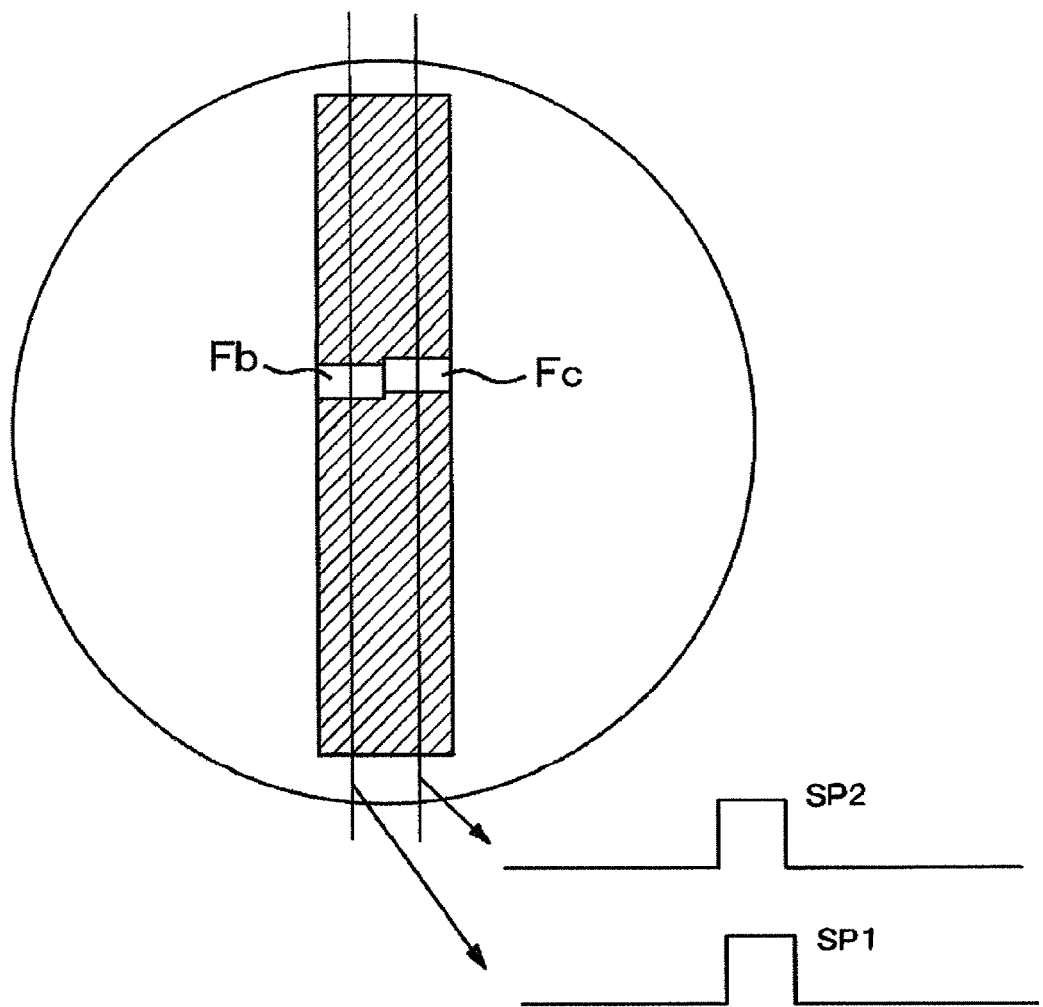
FIG. 14 illustrates a state of observation performed by the second focus detection unit after focusing.

At the time of detecting the position M2 as the local maximum point, the focusing lens 13 is slightly moved towards the position M2b from the position M2. Because the second driving amount from the position at which the local maximum point is detected is calculated in step S14 illustrated in FIG. 10, the focusing lens 13 is driven by a distance of movement from the position M2 illustrated in FIG. 9 slightly towards the position M2b. Thus, the state of observation illustrated in FIG. 12 is changed to that of observation illustrated in FIG. 14. A direction of driving of the focusing lens 13 from the position MN2a illustrated in FIG. 9 slightly towards the position M2b is the same as that of driving of the focusing lens 13, which is performed in step S5. Accordingly, a direction of driving of the focusing lens 13 from a position slightly deviating toward the position M2b from the position M2 is opposite to that of driving of the focusing lens 13, which is performed in step S5.

Thus, especially, when focus correction suitable for the aberration of a human eye is performed, a passive autofocus operation is performed utilizing the contrast of the combination of the focus target images Fb and Fc. Consequently, a high-precision autofocus operation can be achieved.

In the foregoing description of the present embodiment, it has been described that the observing image sensor 20 is used as a focusing sensor. However, it can be considered that, with the flip-up mirror 15 flipped up, the image-recording image sensor 16 is used also as a focusing sensor. Alternatively, the fundus camera can be constructed such that an operator can manually input an instruction via the monitor 34 to perform driving of the focusing lens 13.

As described above, in the present embodiment, at the time of rough focus adjustment by aligning the focus target images Fb and Fc in a line, the active phase difference detection function using the focus target, by which a target value of a driving amount can be calculated, is utilized. On the other hand, at the time of high-precision focus adjustment for performing focus correction suitable for the aberration of a human eye, the passive autofocusing operation utilizing the contrast of the combination of the target images is performed. Consequently, high-speed and high-precision autofocusing can be achieved.

The first exemplary embodiment is configured to cause the focus link mechanism 25 to always interlockingly move the focus target and the focusing lens 13. However, according to another exemplary embodiment of the present invention, upon completion of driving of the focusing lens 13 by the first focus detection subunit 52, only the focusing lens 13 is driven based on a result of detection by the second focus detection subunit 53.

Figure 15:
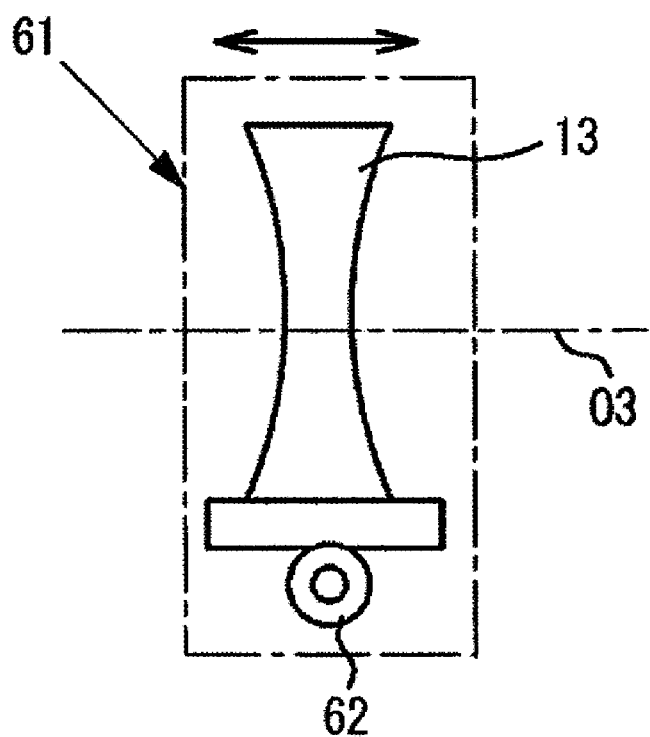
FIG. 15 illustrates a focusing lens unit.

FIG. 15 illustrates a configuration of a focusing lens unit 61. The focusing lens 13 is fixed by the focusing lens moving unit 62, which includes a motor, gears, and the like. The focusing lens moving unit 62 is configured to be movable in the direction of the optical axis O3 based on a control signal output from the control unit 33, independent of the focus link mechanism 25. The focusing lens moving unit 62 is provided separately from the focus drive unit 35, and is connected to the control unit 33.

A second exemplary embodiment according to the present invention is described below with reference to a flowchart illustrated in FIG. 10. As illustrated in FIG. 10, a control process performed in steps S1 to S5 is similar to the process of the aforementioned exemplary embodiment. In step S5, the focusing lens 13 is driven by the focus drive unit 35 via the control unit 33 by a first driving amount calculated in step S4.

According to the present embodiment, upon completion of driving the focusing lens 13 in step S5, in step S10, the detection of the contrast of the combination of the focus target images Fb and Fc is started. That is, when the present embodiment is brought into the state of observation illustrated in FIG. 12, the detection of the contrast of the combination of the focus target images Fb and Fc is performed. Subsequently, processing in steps S11 to S13 is performed similar to the first exemplary embodiment.

At that time, in step S13, it cannot be determined at the determination first made in step S13 whether each contrast value is a local maximum point. Thus, the process proceeds to step S16. In addition, at the first determination made in step S16, the driving of the focusing lens 13 is finished, because the driving of the focusing lens 13 in step S5 is finished in step S10.

Therefore, the process proceeds to step S17. Then, the driving of the focusing lens 13 by a predetermined amount is performed. Subsequently, processing in steps S11 through S13 is repeated. The "driving of the focusing lens 13 by a predetermined amount" is to move the focusing lens 13 while keeping the focus target images Fb and Fc stationary. In addition, the "predetermined amount" is an amount at which the position M2 serving as a local maximum point can be detected.

Figure 16:
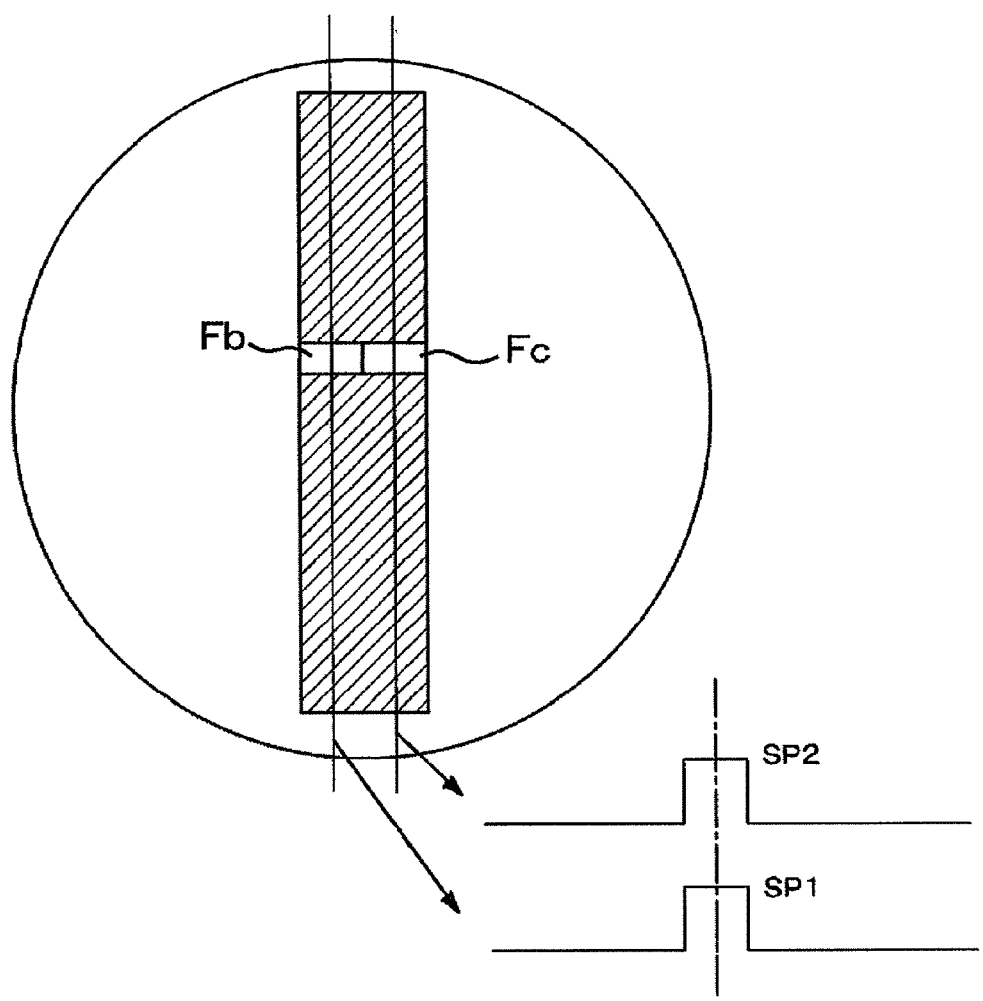
FIG. 16 illustrates a state of observation performed by the second focus detection unit after focusing according to another exemplary embodiment.

Incidentally, according to the second embodiment, a local maximum point, which is the position M2 detected in step S13, may not be detected. Processing to be performed in a case where a local maximum point is detected in step S13 by the driving of the focusing lens 13 by a predetermined amount, which is first performed in step S17, is similar to that in the first exemplary embodiment. Thus, such processing results in an observation state as illustrated in FIG. 16.

A control operation differing from that performed in the first exemplary embodiment is performed in a case where no local maximum point is detected in step S13 even after the process proceeds to step S17 in which the driving of the focusing lens 13 by a predetermined amount is performed, and where the finish of the driving of the focusing lens 13 is detected again in step S16 and the process proceeds to step S17. In this case, as is apparent form the description with reference to FIG. 9, the predetermined amount, by which the focusing lens 13 is driven, is set to be larger than the driving amount first set in step S17 and to correspond to a direction opposite to a direction in which the driving of the focusing lens 13 is first performed in step S17. Thus, a local maximum point, which is the position M2, can be detected. Accordingly, the focusing lens 13 is reciprocatively driven.

Thus, according to the second exemplary embodiment, the contrast is detected by moving the focusing lens 13 while keeping the focus target images Fb and Fc stationary. Change in the contrast is not caused due to the movement of the target projection side unit. Consequently, fine adjustment of the focus can be achieved only by the fundus photographing optical system.

The fundus camera according to the second exemplary embodiment includes a focusing lens moving unit 62 capable of moving the focusing lens 13 in the direction of the optical axis O3 in response to a control signal output from the control unit 33, independent of the focus link mechanism 25. Thus, the detection of the contrast can easily be performed. In addition, even when correction based on the detection of the contrast is performed, the positional relationship between the focus target images observed from an operator does not change. Thus, the second exemplary embodiment has an advantage in preventing occurrence of an uncomfortable feeling.

Figure 17:
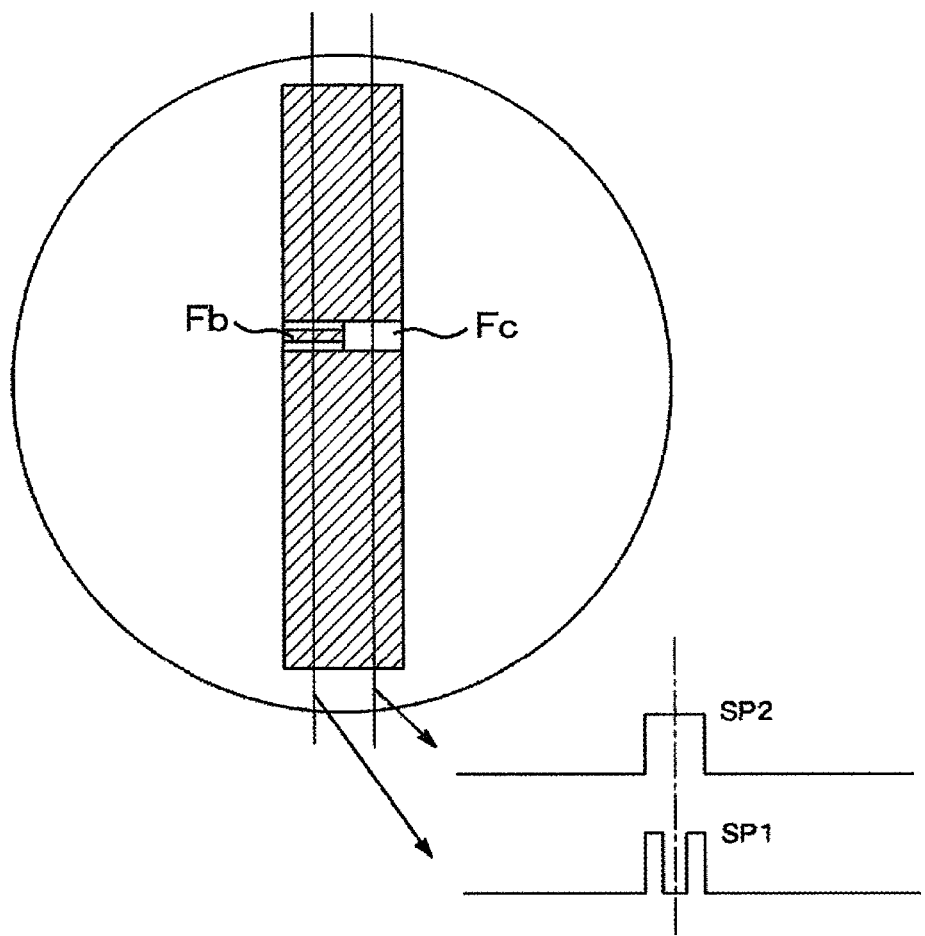
FIG. 17 illustrates a target for improving accuracy in detecting contrast.

In a case where the focus target image Fb having two transmission peaks is used, as illustrated in FIG. 17, the signal SP1 has two peaks. Thus, the detection of the contrast can be accurately performed by the second focus detection subunit 53. Although a change in higher-order frequency components can sharply be extracted by splitting the target into two regions, the contrast of the combination of the target images can be used, instead of extracting high-frequency components.

That is, the focus of the fundus camera on the target image can be detected using the following constant to be calculated using a maximum luminance value Max of the target and a minimum luminance value Min of a middle portion of the target:

$$\text{Contrast} = (\text{Max} - \text{Min})/(\text{Max} + \text{Min}).$$

At that time, the other focus target image Fc has one transmission peak. Accordingly, the first focus detection subunit 52 can be configured to detect a signal SP1 corresponding to a valley between the two transmission peaks concerning the focus target image Fc, and to detect a transmission peak signal SP2 concerning the focus target image Fc. Thus, the distance D can be calculated, based on the positional relationship between the two focus target images.

In addition, the control unit 33 can cause the fundus camera to photograph the fundus upon completion of autofocus based on the contrast of the focus target images.

In a case where initial contrast Mf is equal to or less than a predetermined value, i.e., a case where the focus target images formed on the fundus $E_r$ are affected and deteriorated by an aberration of the subject's eye E or ophthalmopathy thereof, the degree of improvement of the focus of the subject's eye E is low even when focus correction is performed. Accordingly, focus correction is unnecessary. Consequently, the autofocusing based on the detected contrast can be omitted in order to reduce a photographing time.

The fundus camera according to an exemplary embodiment of the present invention utilizes the active phase difference detection function based on the focus target, and utilizes also a change in the target images at the time of high-precision focus adjustment. Thus, high-speed and high-precision autofocus can be achieved. The phase difference detection can easily be achieved by interlockingly moving the focus target and the focusing lens. A fundus can be more accurately brought into focus by the detection of the focus target in best focus using the focus target based on a phase difference.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-122916 filed May 9, 2008, which is hereby incorporated by reference herein in its entirety.

What is claimed is:

1. A fundus camera comprising:
    an illumination optical system including an illumination unit configured to illuminate a fundus of a subject's eye;
    a fundus photographing optical system including an image-recording image sensor configured to capture a fundus image via an objective lens and a focusing lens;
    a focus target located in the illumination optical system at a position conjugate with the fundus of the subject's eye and configured to have a plurality of regions for forming light fluxes respectively passing through different areas of a pupil of the subject's eye to form a plurality of focus target images on the fundus;
an observing images sensor located in the photographing optical system at a position conjugate with the fundus of the subject's eye and configured to capture the plurality of focus target images reflected from the fundus;
a focus drive unit configured to drive the focus target and/or the focusing lens;
a target image position detection unit configured to detect positions of the plurality of focus target images on the observing image sensor;
a first focus detection unit configured to calculate a first driving amount of the focus drive unit based on the positions of the plurality of focus target images detected by the target image position detection unit;
a drive control unit configured to drive and control the focus drive unit based on the first driving amount calculated by the first focus detection unit; and
a second focus detection unit configured to detect a change in the focus target images based on an output of the observing images sensor during a driving operation of the focus drive unit and to calculate a second driving amount of the focus drive unit based on the detected change.

2. The fundus camera according to claim 1, wherein the observing image sensor serves also as the image-recording image sensor.

3. The fundus camera according to claim 1, wherein the focus drive unit drives movement of the focusing lens and that of the focus target images based on a predetermined relationship.

4. The fundus camera according to claim 1, wherein driving of the focusing lens can be performed by a manual operation, and
wherein movement of the focusing lens by a manual operation and that of the focus target are interlockingly performed based on a predetermined relationship.

5. The fundus camera according to claim 1, wherein driving of the focus drive unit by the second focus detection unit is performed using driving of the drive control unit.

6. The fundus camera according to claim 5, wherein the drive control unit uses, when best focus of the focus target image is detected, an amount of driving the focusing lens and/or the focus target to a position, at which the best focus is detected, as the second driving amount calculated by the second focus detection unit.

7. The fundus camera according to claim 5, wherein the drive control unit uses, when best focus of the focus target is not detected, a predetermined amount exceeding a position corresponding to the first driving amount as the second driving amount to be calculated by the second focus detection unit, and detects best focus of the focus target image during driving by the second driving amount.

8. The fundus camera according to claim 1, wherein the second focus detection unit determines, when the focus drive unit reciprocatively drives only the focusing lens, the second driving amount based on contrast of the focus target images during driving of the focusing lens.

9. The fundus camera according to claim 1, wherein the focus target includes two regions formed from light fluxes respectively passing through different portions of a pupil of the subject's eye, and
wherein one of the two regions has a shape including at least two transmission peaks.

10. The fundus camera according to claim 9, wherein the change in the focus target images is based on a luminance of a fundus image formed with a valley between the two transmission peaks.

11. The fundus camera according to claim 9, wherein the focus target includes two regions formed from light fluxes respectively passing through different portions of a pupil of the subject's eye, and
wherein the other of the two regions has a shape including one transmission peak.

12. The fundus camera according to claim 11, wherein a position of a valley between the two transmission peaks of the one of the focus target images and a position of the transmission peak of the other region of the focus target images are used for detection of the positions of the focus target images.

13. The funds camera according to claim 1, wherein photographing of the fundus can be performed after driving of the focusing lens by the second driving amount calculated by the second focus detection unit.

14. A fundus camera comprising:
a fundus photographing optical system including an image sensor configured to capture a fundus image of a subject's eye via a focusing lens;
a focus target projection unit configured to project focus targets onto the fundus of the subject's eye;
a focus drive unit configured to drive the focusing lens;
a first acquisition unit configured to acquire a first driving amount of the focus drive unit based on positions of a plurality of images corresponding to the focus targets; and
a second acquisition unit configured to acquire a second driving amount of the focus drive unit based on contrast of at least one of the plurality of images.

15. The fundus camera according to claim 14, further comprising:
a photographing-starting unit configured to start photographing the fundus in response to a result of driving the focusing lens.

16. The fundus camera according to claim 14, wherein the focus drive unit drives the focusing lens based on the second driving amount after driving the focusing lens based on the first driving amount.

17. The fundus camera according to claim 14, wherein:
the second acquisition unit acquires the second driving amount of the focus drive unit based on the contrast of the plurality of images while and/or after the focus drive unit is driving the focusing lens based on the first driving amount.

18. The fundus camera according to claim 14, further comprising:
a photographing-starting unit configured to start photographing the fundus after the focus drive unit drives the focusing lens based on the second driving amount.

19. The fundus camera according to claim 14, wherein the focus target projection unit configures to have a plurality of regions for forming light fluxes respectively passing through different areas of a pupil of the subject's eye, and wherein the image sensor configures to capture the plurality of images.

20. The fundus camera according to claim 14, further comprising: a contrast detection unit configured to detect at least one of an intensity, an edge, and frequency components of at least one of the plurality of images, and to detect the contrast based on a result of the detection.

21. A ophthalmologic apparatus comprising:
a focus target projection unit configured to project focus targets onto a subject's eye;

a photographing optical system including an image sensor configured to capture a plurality of images corresponding to the focus targets via a focusing lens;

a focus drive unit configured to drive the focusing lens; and an acquisition unit configured to acquire at least one of a driving amount and a driving direction of the focus drive unit based on contrast of at least one of the plurality of images.

22. The ophthalmologic apparatus according to claim 21, further comprising: a contrast detection unit configured to detect at least one of an intensity, an edge, and frequency components of at least one of the plurality of images, and to detect the contrast based on a result of the detection.

23. The ophthalmologic apparatus according to claim 21, wherein the focus drive unit drives the focusing lens based on at least one of the driving amount and the driving direction after driving the focusing lens based on positions of the plurality of images.

* * * * *